United States Patent [19]

Hall et al.

[11] 4,396,139

[45] Aug. 2, 1983

[54] SURGICAL STAPLING SYSTEM, APPARATUS AND STAPLE

[75] Inventors: Richard W. Hall, New Canaan, Conn.; Ingram S. Chodorow, Upper Saddle River, N.J.; J. David Dainow, New York, N.Y.

[73] Assignee: Technalytics, Inc., Upper Saddle River, N.J.

[21] Appl. No.: 121,813

[22] Filed: Feb. 15, 1980

[51] Int. Cl.³ .............................................. B31B 1/00
[52] U.S. Cl. ...................................... 227/19; 72/410; 72/334 R; 72/83; 72/156
[58] Field of Search .................... 128/334 R, 325, 335, 128/346; 227/DIG. 1, 19, 120, 83, 82, 156; 411/457, 458, 459, 460; 72/409, 410

[56] References Cited

U.S. PATENT DOCUMENTS

| | | | |
|---|---|---|---|
| 2,396,203 | 3/1946 | Robinson | 128/325 |
| 3,231,976 | 2/1966 | Wallshein | 227/DIG. 1 |
| 3,873,016 | 3/1975 | Fishbein | 227/DIG. 1 |
| 3,945,238 | 3/1976 | Eckert | 227/DIG. 1 |
| 3,958,576 | 5/1976 | Komiya | 227/DIG. 1 |
| 4,202,480 | 5/1980 | Annett | 227/DIG. 1 |

*Primary Examiner*—Paul A. Bell
*Attorney, Agent, or Firm*—J. David Dainow

[57] ABSTRACT

A surgical stapling system, apparatus and staple wherein a resilient staple has a relaxed closed configuration, is expanded into an open crescent shape, and finally is allowed to return to its closed configuration while simultaneously piercing and drawing together adjacent edges of an open incision or wound. The stapling apparatus contains a plurality of staples and includes projections which engage and secure each staple to the apparatus until its closure to tissue is complete and separation from the apparatus is desired. Further mechanism is provided to control the staple as it closes and optionally to re-open a closed or partially closed staple.

22 Claims, 27 Drawing Figures

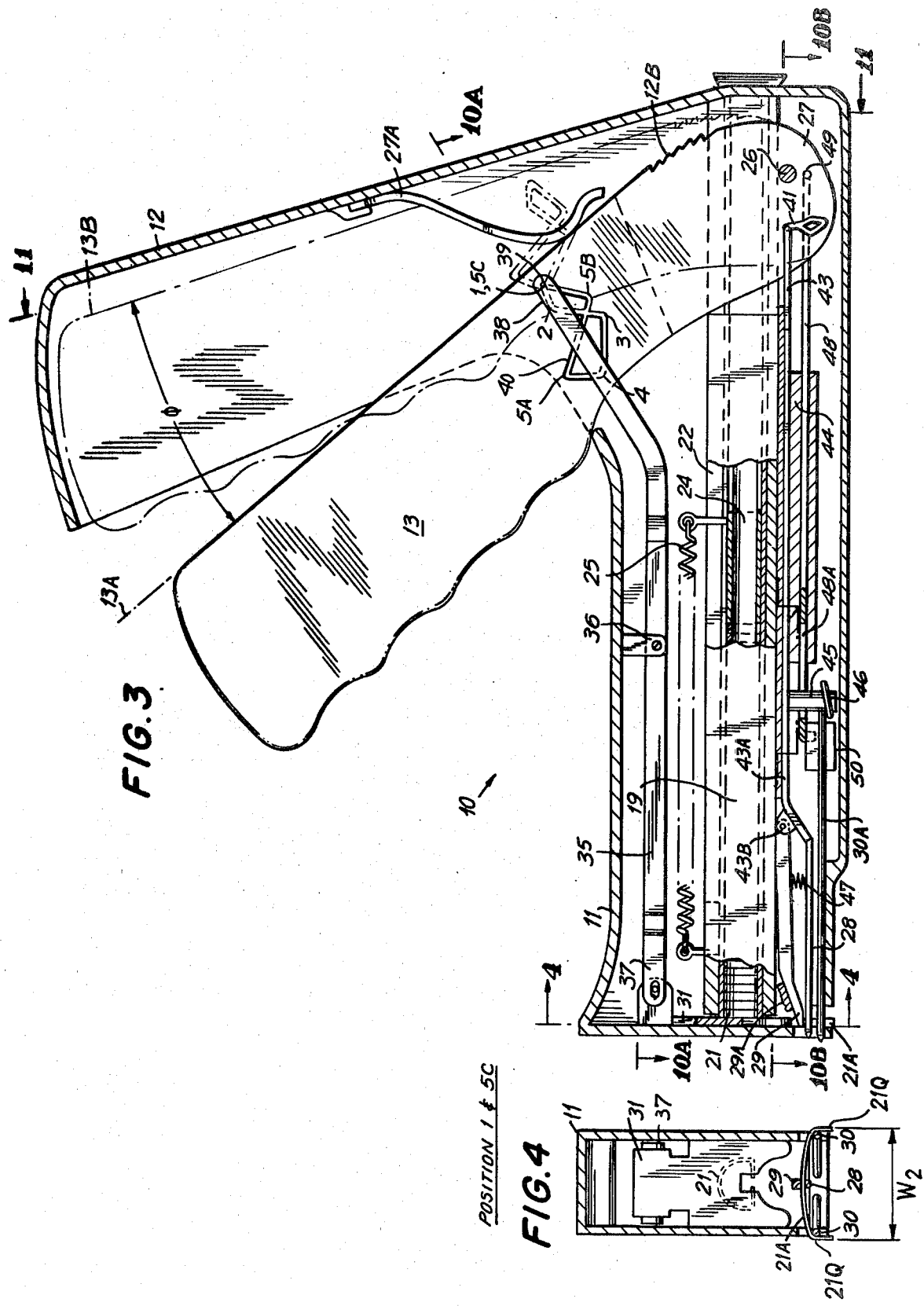

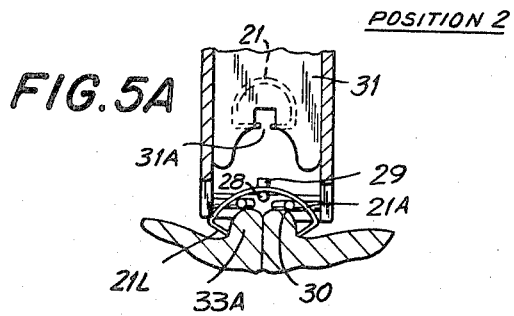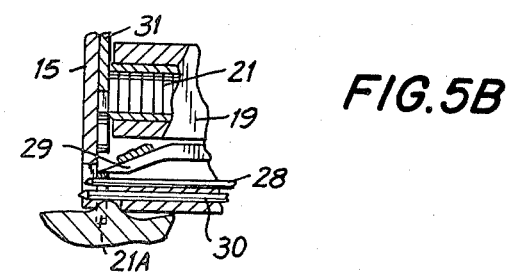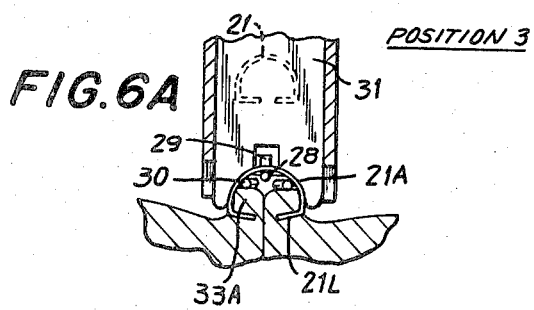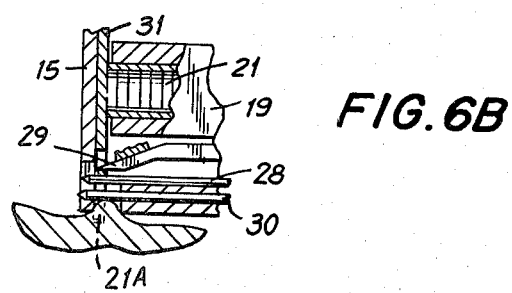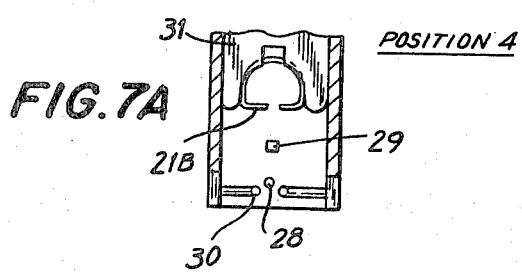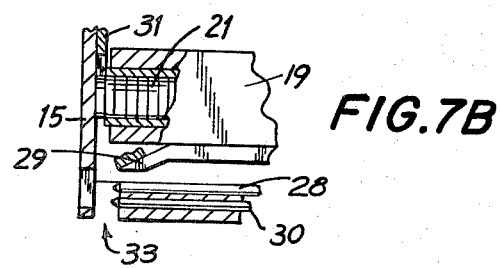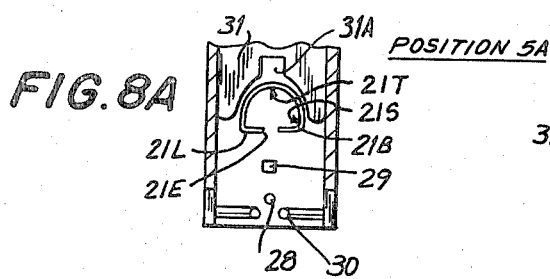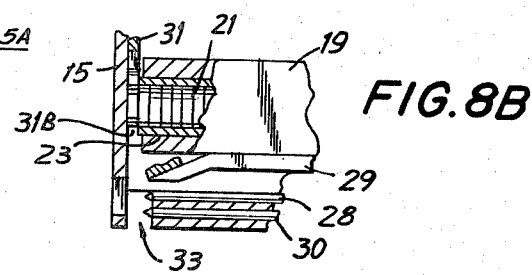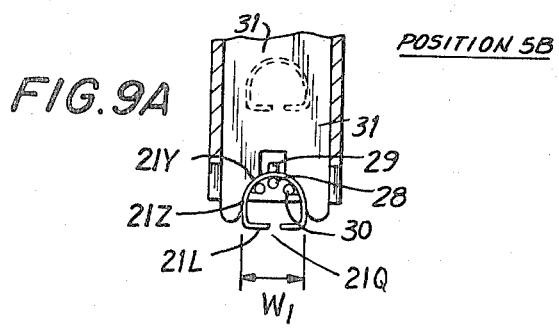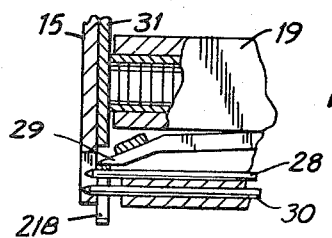

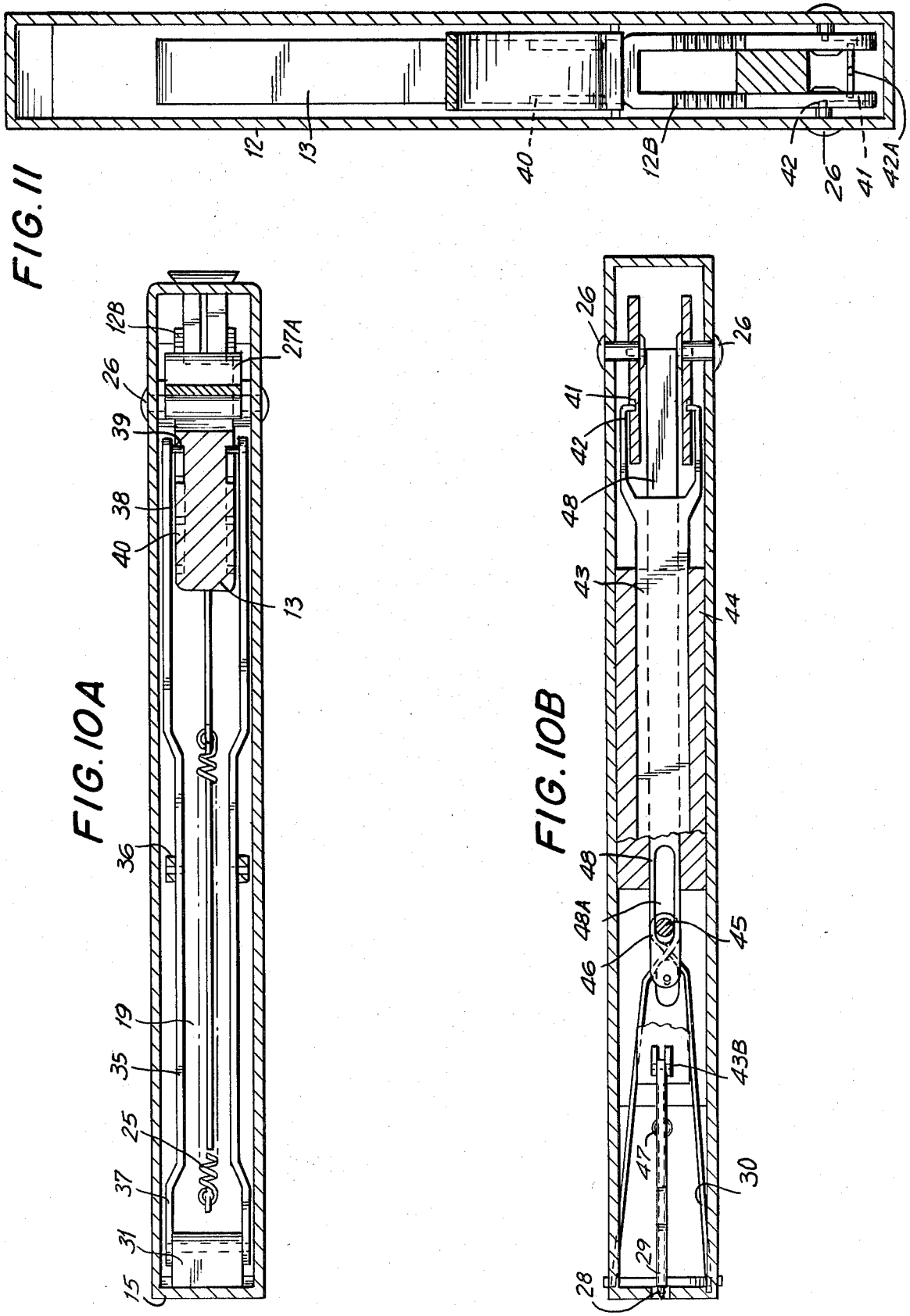

SURGICAL STAPLING SYSTEM, APPARATUS AND STAPLE

BACKGROUND OF THE INVENTION

This invention concerns closure of incisions at the conclusion of many typical surgical procedures. Such closures can involve the rejoining of a wide variety of tissue types and bones, such as the rib cage, fascia, muscle skin and fat. Primary objectives of these closure procedures are to affect rapid and proper healing with a minimum of discomfort and scarring and to ensure that the wound remains securely closed. A related objective is that the closure not interfere with subsequent bandages and change of dressing.

Closure generally involves joining various layers of tissue, each in a special and correct manner. For instance, in abdominal surgery the severed peritoneum layer must be joined, followed by the layers of muscle, fascia, fat and skin. Additionally, retention sutures which pass through all layers may be used or required as insurance that the closure will not open. To accomplish these sutured closures typical materials include silk, gut and a wide variety of synthetics including Dacron ®, Teflon ® and various new disposable materials. Depending on strength required, the material may be monofilament or braided and the caliber may be varied. Also there are metal sutures which are usually made from non-reactive stainless steel. Each material has characteristics which make its use appropriate for a specific purpose.

In all these techniques an important consideration is scar formation, the manner in which the human body reacts to suture materials which behave, for the most part, as foreign bodies and cause the body's defense mechanisms to seal them off with connective tissue. When the body's reaction is greater, more scar tissue will be formed.

Obviously, sutures cannot be passed without a delivery system which for these sutures consists of a large assortment of needles. Each type of needle is designed to provide a particular function, such as ease of handling, ease of passage, ease of release, minimal trauma, etc. The surgeon will generally either thread a needle or use pre-threaded suture-needle combinations and secondary instruments such as suture holders.

Wound closure is thus a major concern among surgeons whose primary objectives include: (a) to minimize time required to close, (b) to reduce surgeon fatigue and patient anesthesia time, (c) to reduce tissue trauma and accelerate wound healing, (d) to minimize blood loss, (e) to achieve optimum cosmetic results, and (f) to control and reduce overall costs.

It is these objectives which led to the development of a relatively new method of closure, namely joining adjacent tissue with metal staples delivered and secured by a staple gun. These metal staples which have partially replaced traditional sutures, have becomes popular for both external and internal closures, including joining cut ends of blood vessels, hollow organs and various layers of tissue within the body. Dozens of stapling devices for surgery have been developed by Americans and others, especially those of the Soviet Union.

One aspect of virtually all of these known stapling devices is the characteristic way in which they function and the use of bendable but non-resilient metal staples. Force is applied to change the initially open, generally U-shape configuration of each metal staple to a final, closed configuration, whereby the staple will hold two adjacent edges of tissue together. The staple devices are held and operated by the surgeon's hand, with force applied either manually by the surgeon or by a power-assisted mechanical force incorporated into the stapler. The force required to bend or crush the ends of the non-elastic metal staples is substantial, and is typically applied by a driver which drives each staple into position and then forcibly bends the legs of the staple. Once placed, the staples cannot be removed without the use of a separate device which forcibly returns the staple to its generally open configuration, so that removal is possible without tearing the tissue.

It is the broad purpose of this present invention to provide a surgical stapling instrument for joining with staples two opposing layers of tissue, skin and/or fascia of a patient. This device is to utilize a new type of elastic or spring staple and a unique delivery system, and to have a mode of increased control including reversible operation for removing an emplaced staple with the same device and without even moving the device from the site of placement. Another object of the present invention is to achieve a reduction in overall size and weight of the stapler in order to provide more exacting control for the surgeon, especially in difficult-to-reach places. A further objective is to reduce the amount of manual force and motion applied to the device when it is at the site or delivery point of the staple.

The new invention disclosed and claimed in subsequent sections of this application is fundamentally different from all known prior art stapling systems and devices, with typical of such prior devices being disclosed in the U.S. patents listed in the Appendix I attached hereto, and all relating to non-elastic staples which are crushed from open to closed condition.

SUMMARY OF THE INVENTION

The present invention is a hand-held and hand operated multi-stage surgical instrument that carries a plurality of new spring staples, preferably in a cartridge, and delivers and closes one staple at a time to the adjacent edges of an incision being closed or adjacent tissue or other substances being joined. Although the new staples are similar in size to standard non-elastic staples of known staple-guns, the new staples are different in many important ways. The new staples are flexible and resilient with sufficient memory to permit rather extensive alteration of the staple's shape when force is applied to open the staple for emplacement, while allowing the staple to return to its original closed configuration in a state of rest. Each of the staples has a shape which is the ideal for its final position in place in the body when it joins two layers of tissue. The staples are initially loaded in a cartridge or magazine, wherein they have the same configuration that they will be assuming when finally placed in an incision.

Because of these structural characteristics the staple itself provides a large portion of the force required to return to its closed shape and thereby pull adjacent tissues together and achieve proper closure. Accordingly, less force is required by the operator than with prior art staples and stapling devices, where each staple must be forcibly bent beyond its elastic limit for each step of closure. The new delivery system therefore may be smaller and lighter which permits better control, better visibility, and less fatigue on the part of the surgeon.

This device is operated by squeezing and pivotting a trigger a selected distance toward or into the handle, and subsequently releasing the trigger to automatically return to its normal position. This motion of the trigger activates a multi-stage operation that includes the following steps: (a) loading a staple from the staple magazine into the placement section; (b) opening or expanding the staple within the placement section; (c) delivering the open staple so that its ends contact the adjacent edges of tissue of the incision; (d) releasing the staple on a fully controlled basis into the tissue; (e) providing a modest amount of force to guarantee that the staple fully closes, i.e. returns to its original configuration, (f) releasing the staple from the device; and (g) re-loading a new staple into the placement section.

The advantages of this device over the known prior art devices are many. As mentioned above the staple's own resilient force urging it to a closed configuration reduces to a minimum any additional manual force required of the surgeon. Also the distance the surgeon's fingers must depress the squeeze-action trigger is very short. Thus the new device is essentially "easy" to operate, requires little effort, and has no jolt or comparable motion upon closure or release of each staple. The handle of one preferred embodiment of the device extends upward from the body part as contrasted with prior art staple guns where the handles extend downward or rearward, below or behind the device. The design of this embodiment provides better visibility of the closure area since the space below the body of the device is clear of a handle protrusion and clear of the surgeon's hand. Also this design eliminates the problem in some prior art devices where a downward handle forces the device to be tipped upward in order to have its staple discharge-end adjacent the incision.

Another major and significant improvement provided by this invention is its ability to remove a staple after such has been placed, if the surgeon determines the staple has not been placed properly or the surgeon decides for any other reason to immediately remove the staple. This is permitted by the creation of an indicator or other signal in the trigger assembly that tells the surgeon when the staple has been placed and fully closed in the incision, but not yet released from the device. If he is satisfied with the placement he merely continues to squeeze the trigger beyond the indicator point and the placement and release are concluded. If, however, he wishes to withdraw the staple, he simply releases the trigger, which is spring-biased to return to its open or start condition; the staple remains tied to the device, is opened and removed from the tissue, and is ready to be re-positioned on the incision and inserted.

In all other known prior art stapling devices, once the stable has been placed, correctly or incorrectly, it may only be removed by a secondary or separate device. The reversibility capability of the new stapler permits a margin for error and enables instant correction or change of plan on the part of the surgeon.

Another important feature is the jam-free mechanism which prevents loading of a new staple until the previous staple has been fully released from the instrument. The loading function is accomplished during the return phase of the trigger and cannot therefore be activated until the indicator point has been passed by the trigger during the the staple-displacement phase.

All functions of the device (loading, opening, placement, closure and release) are accomplished as part of a continuous mechanical action, namely squeezing and then releasing the trigger. This device has very few moving and stationary parts, which assures simplicity and problem-free operation and low production costs to create the possibility for this system to be a single-use disposable product.

Because there is no requirement for converging jaws or for a crushing force to close non-elastic staples around a driver as in the prior art, the width of the new device may be very small, approximately the width of one new staple in its open position. This narrow configuration is most useful, of course when skin stapling is required in relatively inaccessible areas.

Removal of the new staple requires a simple opening or expansion of the resilient staple. Above and below the mid-section of the staple are locking and safety pins respectively which engage and secure the staple to the device until final release. While these two pins remain engaged to an otherwise emplaced staple, a pair of expansion pins adjacent the safety pin at the lower surface of the staple are caused to diverge and thereby expand the generally oval shape of the staple, causing the legs thereof to separate. In this way the staple is changed from a generally oval shape to a generally U-shape, so that it can be easily and safely withdrawn from the incision tissue.

A semi-automatic nature of the device is provided by three springs or spring members. A first main spring urges the trigger outward from the handle, the force of this spring being overcome relatively easily by manual squeezing of the trigger by the surgeon. A second spring, such as a constant tension coil Negator® spring, urges the staples in the magazine toward the discharge end, where a single staple is discharged periodically and driven by a driver to a "ready" position to be subsequently expanded, emplaced in the incision, and finally released. A third spring is inherent in the expansion pin member whereby a resilient member has a pair of adjacent pin-like parts which are normally in closed position, and may be forced apart by a wedge movable between the pins. These pins will resiliently converge when the wedge is removed.

To cause proper movement of the driver and the safety, lock and expansion pins, two cams are provided on the trigger which actuate drive levers when the trigger is squeezed clockwise and subsequently released to spring back counterclockwise. The first cam establishes the motion pattern for the driver to deliver staples and later to apply the final closing force on each staple. The second cam establishes the motion pattern for the safety, lock, and expansion pins to move forward and rearward together at the proper time. A separate wedge is driven by a direct linkage with the trigger to open and close the expansion pins. Accordingly, squeezing of the trigger automatically operates the device through its various stages for loading a staple from the magazine into the placement section, expanding the staple, delivering the open staple to the wound, allowing the staple to engage and close the wound, and final releasing of the staple, or optionally re-opening and removing the staple.

The new stapler as disclosed herein has many features which are significant and useful when used in the combination described above or in various other combinations. The new invention comprises first, a new elastic staple that is resiliently expanded to engage adjacent edges of tissue and subsequently released to close and secure the tissue. The invention further comprises a delivery system or apparatus to contain the staples, and to expand, deliver, and release them as required, without having to use a crushing force. The next and most significant feature is the ability to easily, quickly, and safely reverse the staple emplacement process and thus to remove the staple with the same device. In the preferred embodiment of this invention the staple remains secured to the staple gun by a safety pin even while the staple has penetrated the tissue and closed, thus affording the surgeon constant and total control of the stapling procedure and apparatus.

To produce the proper movement patterns of parts for delivery, opening, closing etc. of the staples many different mechanisms may be devised; however, the preferred embodiment disclosed herein is not only remarkably simple to manufacture and use, it is designed to be extremely inexpensive to produce, while still meeting all the objectives described in earlier paragraphs. This preferred embodiment is illustrated in the appended drawings and described in the following paragraphs.

BRIEF DESCRIPTION OF THE DRAWINGS

FIG. 3 is a side elevation view thereof taken in section along lines 3—3 in FIG. 2;

FIG. 4 is a front end elevation view thereof taken in section along line 4—4 in FIGS. 2 and 3;

FIGS. 5A, 6A, 7A, 8A, and 9A are front end elevation views similar to FIG. 4 and showing with FIG. 4 the sequential stages of operation of the invention;

FIGS. 5B, 6B, 7B, 8B, and 9B are fragmentary side elevation views corresponding to FIGS. 5A-9A respectively;

FIGS. 10A and 10B are generally horizontal sections taken along lines 10A—10A and 10B—10B respectively in FIG. 3;

FIG. 11 is a generally vertical section taken along line 11—11 in FIG. 3;

DESCRIPTION OF THE PREFERRED EMBODIMENT

Figure 1:
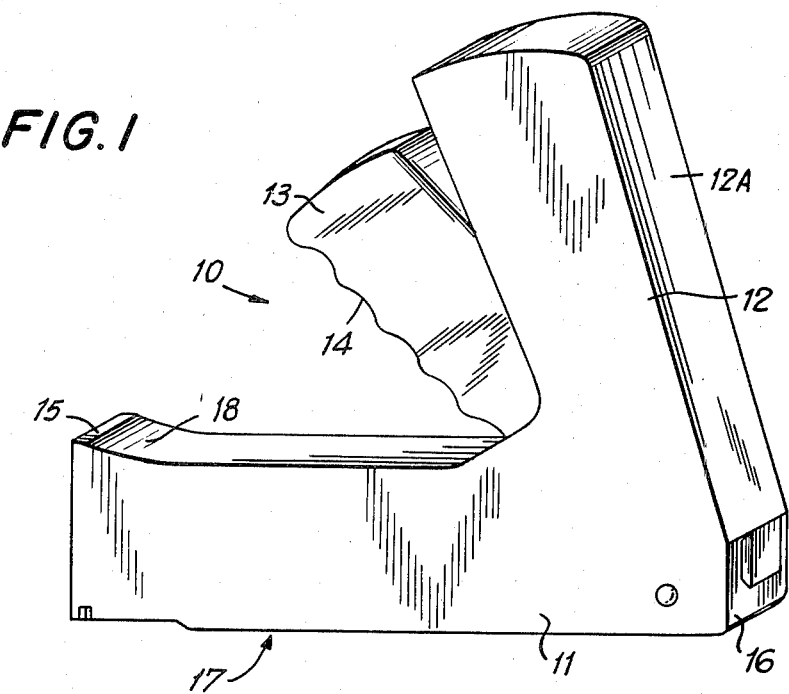
FIG. 1 is a front perspective of the new invention.
Figure 2:
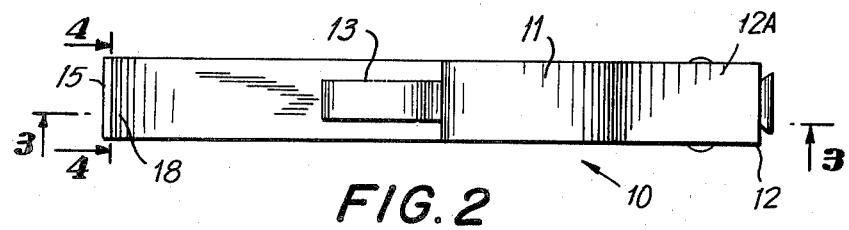
FIG. 2 is a top plan view thereof.

FIG. 1 is a perspective representation and FIG. 2 is a top plan view of the new stapler 10 which includes a main housing or body 11, a handle portion 12 which extends generally upward and at a slightly forward angle from the body portion, a rear part 12A of the handle, a movable trigger part 13 which can be squeezed and compressed into handle 12, and curved finger-receiving portions 14 of the trigger 13 for more securely gripping this device. The basic housing 11 has a front end or face plate 15, a rear end 16, a lower portion 17 of the front end, and an upper portion 18 of the front end.

Figure 3A:
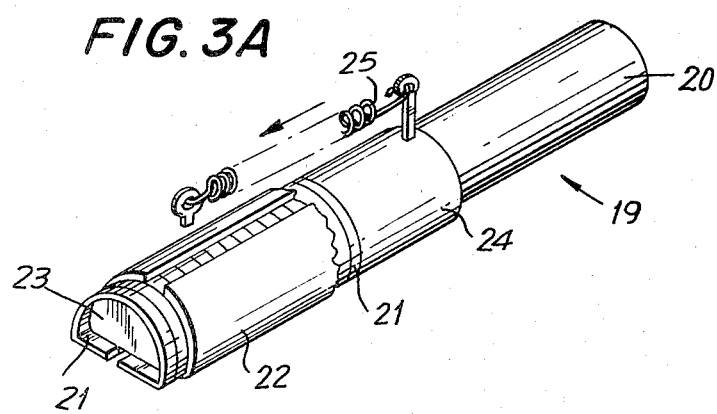
FIG. 3A is a fragmentary front perspective view of the staple magazine.

FIG. 3, as a sectional view of FIG. 2, illustrates the basic internal parts of the new staple delivery system for delivering, closing or opening staples as desired by the surgeon. Within the housing is a magazine 19, also shown in FIG. 3A, which can contain and carry approximately 100 staples in its approximately 4 inch length, the magazine comprising a bar 20 extending horizontally on which the staples 21 are aligned side by side. A hood or outer sleeve 22 is used to guide the staples as they move along the bar toward the forward end 23 thereof, and a pusher 24 aligned with the staples on bar 20 is driven by spring 25 which urges staples along the bar for delivery into a staple discharge area whenever the staple device is actuated.

Additional operational elements contained within the housing 11 and partially within the handle 12 are illustrated in FIG. 3. The trigger 13 pivots on axle 26 with a lower section of the trigger 27 extending below the pivot axle. The trigger is pivotable between a first open position 13A to a fully closed position 13B shown in dotted line which defines therebetween about 30° of movement. This same movement obviously occurs below the pivot axle as above. A spring symbolized by item 27A constantly urges trigger 13 counterclockwise into its open position 13A. In use the surgeon grips the handle 12 with his palm on the back part 12A and his fingers on the front part around finger grip portions 14. Squeezing and releasing the trigger is the only requirement for all operations of this device.

First we will describe what happens to each staple as it is expanded and delivered, directed to engage and close an incision, and then becomes released from the device; in later paragraphs we will describe what internal sub-assemblies of the mechanism are responsible for this sequence of operations. The various steps or positions of operation of the device and the corresponding changes of the staples configuration will be designated positions 1, 2, 3, 4, 5, 5A, 5B, 5C, which are illustrated in FIGS. 4–9B. In position 1 a staple 21A is alreadly expanded and positioned for delivery to an open wound. This staple is secured and stabilized by lock and safety pins 29 and 28 respectively above and below the mid-portion of the staple as indicated in FIG. 4; the staple is held open and expanded by expansion pins 30. Also in this first position driver 31 is in its mid-height position whereby it covers the end of magazine 19 and prevents additional staples 21 from being discharged from the magazine. It can be seen in FIGS. 6A and 9A that the driver has low positions, and in FIGS. 7A and 8A the driver has high positions. A notch 31A in the center portion of the driver provides clearance space when the driver descends, for the lock pin 29 as indicated in FIG. 6A.

Now proceeding to FIGS. 5A and 5B it can be seen that the expansion pins 30 have moved together to their closed position, the staple 21A has resiliently started to return to its naturally closed position; the driver 31 has remained in its mid-position and the four pins, namely the lock pin 29, the safety pin 28 and the expansion pins 30 have remained in their extended position which means they are fully to the left in the corresponding FIG. 5B and also in FIG. 3.

Figures 19, 20:
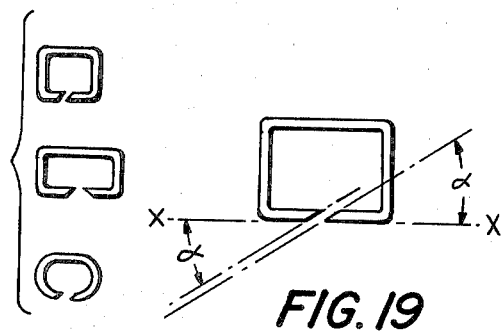
FIG. 19 is an elevation view of three additional staple embodiments.
FIG. 20 is an elevation view of a staple showing a detail of its ends.

Now moving to position 3 illustrated in FIG. 6A, it is seen that the driver 31 has descended further, has engaged the staple 21A and forced it into a fully closed loop wherein the leg portions 21L of the staple are almost co-linear shown on axis X—X in FIG. 19. In this position 3 the four pins mentioned above continue to remain in their fully extended state.

In moving from positions 3 to 4, the driver 31 begins to rise and simultaneously the pin assembly begins to move backward, which is to the right in FIG. 7B. More particularly the lock pin 29 begins to rise away from the safety pin 28, whereby the staple which was closed in FIG. 6A, is then free to be separated from the stapling device 10. When position 4 is fully reached, the pin assemblies are fully retracted and the driver 31 has risen to the point where it almost exposes the next staple 21B in the magazine to be discharged; however an edge 32 of the driver jaw still covers the next staple 21B and prevents it from moving forward until the proper time.

In the next phase of operation as indicated in FIGS. 8B and 8A, the driver 31 is moved to its highest position, thus exposing the magazine to deliver one staple 21B into the space 31B between the end 23 of the magazine and the face plate 15 of the housing. Also during this step the pin assemblies remain retracted. The next position 5B as illustrated in FIGS. 9A and 9B shows that the driver 31 has descended and in so doing has driven the staple 21B downward to its waiting position, and simultaneously the pin assemblies have moved forward with the locking pin 29 and safety pin 28 fully engaging and gripping the staple, and with the expansion pins 30 also moved forward but remaining in their closed positions beneath the center section of the staple. Thus the staple has been delivered in its fully closed, natural and relaxed state. The final position 5C is also the beginning position 1, where the driver has risen slightly, the pin assemblies remain extended, and most significantly, the expansion pins 39 have diverged thereby opening the staple to its ready condition.

The staple illustrated in FIGS. 4, 5A, 6A, 7A, 8A and 9A has a generally semi-circular shape, by virtue of the staple wire formed into a configuration that circumscribes a space that is generally semi-circular. This staple shape comprises top 21T and side 21S parts forming an arch and a bottom or base part as legs 21L whose ends 21E extend generally toward and closely adjacent each other when the staple is in its relaxed, closed state. When this staple is opened it takes on a generally crescent shape as shown in FIGS. 5A and 4, with the legs extending generally downward and oblique to their relaxed orientation and the ends of these legs moved apart and less closely adjacent to each other than in the relaxed state.

Now we will explain what parts of the trigger and drive mechanisms cause the driver and the pin assemblies to move in the motion paths described, and cause the staples to be opened and closed.

Figure 14:
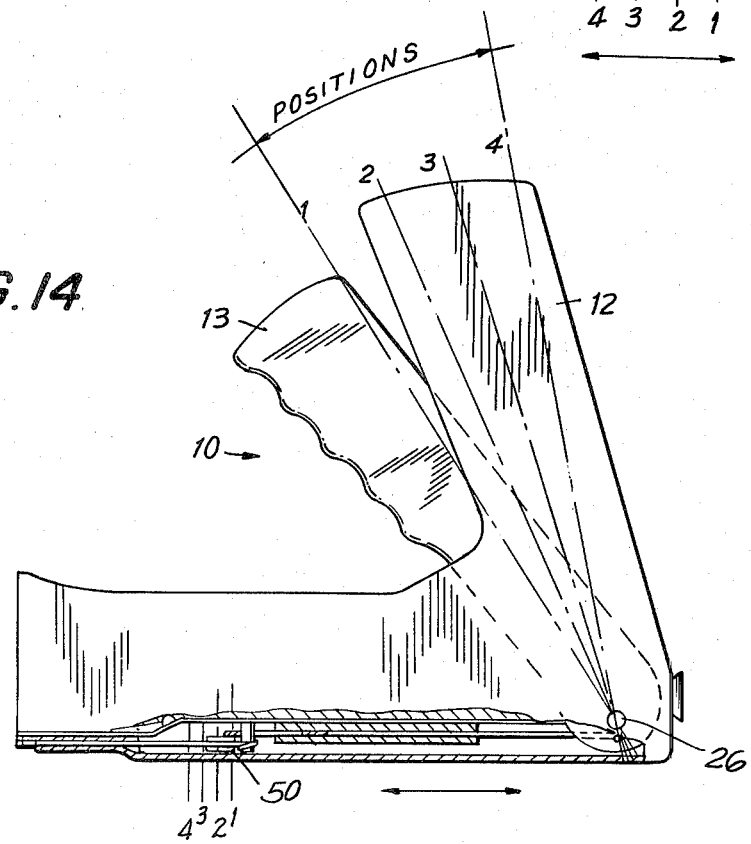
FIG. 14 is a schematic side elevation view showing the handle and expansion pin lever in different positions.

As indicated in FIGS. 3 and 14 the trigger 13 is movable from its first and open position 13A in a clockwise direction to position 13B. It is intended that when the trigger is in this open position, the driver will be up and the staple will be expanded and ready for delivery to an incision as shown in FIG. 4. The logical sequence in the operation of this device is for the surgeon to slowly squeeze the trigger into the handle when he wishes to deliver a single staple which is to engage and pierce the adjacent layers of tissue and close that portion of the wound. Accordingly, the discharge opening 33 (FIGS. 7B and 8B) is placed near and directly above the adjacent and closely approximated edges of the tissue 33A, as shown in FIGS. 5A and 6A. Slowly squeezing the trigger will cause the expansion pins 30 to converge and allow the staple to begin to close according to its own resilience which urges it toward its naturally closed position as indicated in FIG. 5A. If the resistance of the tissue is not too great the points of the staple will pierce the tissue and continue to penetrate the tissue as the staple finds its natural totally closed position.

As the surgeon continues to squeeze on the trigger the driver will begin to descend until it engages the top surface of the staple as indicated in FIG. 6A and urges the final closure of any staple which has not found its own fully closed position. At this time of final closure when the trigger is approaching position 4, the device will emit a signal such as (a) a sound caused by a ratchet 12B engaging spring 27A within the handle, or (b) a higher trigger resistance caused by a spring-biased detent or other device. The indicator will warn the surgeon that the staple is fully closed, that the pin assemblies are still forward and still engaging and locked to the staple, and that further compression of the trigger will release the pins from the staple. The signal furthermore tells the surgeon that if at this time he decides the staple should be removed for any reason, he can simply relax his grip on the trigger and the initial steps described above will operate in reverse, namely that the pin assemblies will remain engaged and locked to the staple, except that the expansion pins will start to diverge and slowly open the staple, carrying it from positions 4 to 3 to 2 to 1, until the staple is fully open and removed harmlessly from the wound. Such removal will occur without damaging tissue, without requiring the surgeon to move the stapling device away from the wound, and without requiring any separate and/or additional device for the removal of the staple.

If the surgeon, upon sensing the signal indication mentioned above, decides the staple is properly placed and satisfactory, then he would simply continue to squeeze the trigger to its final compressed condition 13B, whereby the pin assembly will have reached position 4 indicated in FIGS. 7A and 7B, the staple will be released, and the driver will begin to rise. After the trigger is fully squeezed and the staple is released and separated from the staple gun, the surgeon begins to relax his grip on the trigger which is spring-biased to return to first position 13A while the driver moves through position 5A, 5B, and 5C (same as 1) as indicated in FIGS. 8A, 9A and 4. When the trigger has fully returned to its initial position 13A, a new staple will be opened and ready as indicated in FIG. 4 where the staple's maximum width between its two legs, namely between opposite corresponding parts of its two legs, is wider than the width of the housing adjacent said opened staple.

What has happened during the return of the trigger phase, is that the driver has risen to its highest position shown in FIG. 8A exposing the next lead staple 21B; the driver then descends as indicated in FIG. 9A driving the staple down to its ready position, and simultaneously the pin assemblies move forward and grip the staple 21B with the expansion pins in their closed position. In the last degrees of motion by the trigger returning to position 13A, the expansion pins open while the safety and lock pins remain tightly gripped at the midpoint of the staple and this ready position is shown in FIG. 4 which is the same as position 1.

The drive assemblies for the driver and the pins are quite simple and require few parts, as shown in FIG. 3, 10A, 10B, and 11. For driving the driver there is a lever arm 35 which is pivotable about pivot joint 36, has a remote end 37 pivotally engaging the driver 31 and a near end 38 which includes at its end a follower 39 which moves in cam groove 40 defined in a portion of the trigger 13. It should be obvious that movement of the trigger in one direction or another will cause the follower 39 to traverse a path defined by the cam groove 40; this in turn will drive the near end arm 38 of lever 35 about pivot 36 and cause a similar but opposite motion to the remote end 37 and the same motion to driver 31.

A second cam 41 is also shown at the bottom right portion of FIG. 3, this cam also being situated in or on some portion of the trigger 13. A cam follower 42 rides in the cam groove 41, this follower being carried by lever 43 which moves axially in guide 44. Accordingly, as the trigger pivots, the follower 42 is driven to follow the shape of cam 41 and cause a corresponding motion of projection 45 extending downward from lever 43 into the rear loop 46 of the expansion pin body 30A, see FIG. 12. Link 43 has a front portion 43A that includes pivot 43B and a forward extension forming safety pin 28. Coupled to pivot 43B is lock pin 29, with a spring 47 urging pins 28 and 29 apart, and a guide 29A directing lock pin 29 diagonally downward whenever it is urged forward by lever 43.

The purpose of this last sub-assembly is to link together the lock pin 29, the safety pin 28, and the expansion pins 30 into a unit that moves forward or rearward depending upon the guiding control of cam 41. This explains why, in the sequence of positions 1-5 described earlier, the four pins always move forward and rearward together, and why the lock pin in its upper position can permit passage of the staple from above to below the lock pin as shown in FIGS. 7B and 8B, while the lock pin later descends down on top of the staple and locks it with the safety pin as indicated in FIG. 9B. Below lever 43 is a generally parallel lever 48 coupled at 49 to the lower part 27 of the trigger and movable axially to drive wedge 50 which appears also in FIGS. 10B, 12 and 14. The wedge is driven forward directly by pivoting of the trigger. In FIG. 14 positions 1-4 correspond to the same positions in FIGS. 4-7B, so that with open position of the trigger the wedge is rearward at position 1 in FIGS. 12 and 14, thus causing the expansion pin member 30A to open and pins 30 to diverge for opening a staple as shown in FIG. 4. Squeezing the trigger drives wedge 50 forward to positions 2, 3, and 4, according to FIG. 12; in these forward positions the expansion pins 30 remain closed and inactive, as shown in FIGS. 6A-9A. In FIGS. 3 and 10B the lever 48 that drives wedge 50, includes a slot 48A that allows clearance for projection 45 to extend through while lever 48 reciprocates.

Figure 15:
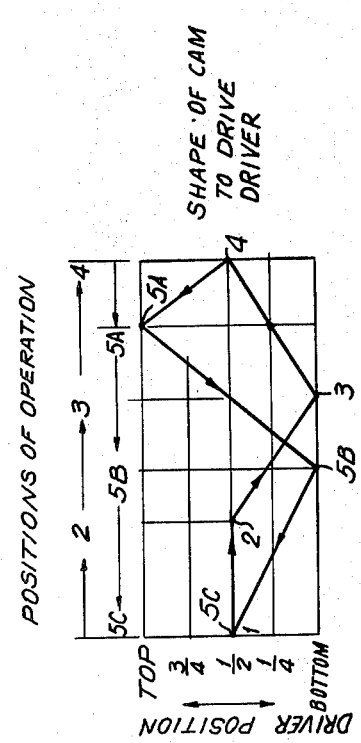
FIG. 15 is a graph showing a cam configuration for the sequential movement of the trigger and corresponding driver movement.

The precise motion pattern of the driver 31 and the four pins is established by cams 40 and 41, explained more fully as follows. FIG. 15 is a graph illustrating the coordinated action of the trigger and driver, as indicated in "Positions of Operation" 1, 2, 3, and 4 across the top from left to right, and positions 5A, 5B, and 5C from right to left. The vertical direction indicates the movement of the driver from its bottom position to its top position with intermediate $\frac{1}{4}$, $\frac{1}{2}$ and $\frac{3}{4}$ positions. At successive points in the figure "8" shape in FIG. 15 representing the cam groove 40 of FIG. 3, there are the positions 1 through 4, and 5A through 5C repeated for clarification. An examination of this graph indicates that as the trigger moves from position 1 to position 2, namely moving clockwise as it is being squeezed, the driver is intended to follow the pattern of the cam, and accordingly it moves from position 1 to 2 in the graph and does not change its elevation from the half-way position. Next the trigger moves from position 2 to 3 and the cam shape and driver position moves from 2 to 3 which indicates that the driver descends from its half-elevated position to its down position 3. Further, compression of the trigger from 3 to 4 causes the driver to move back up to its half-position as indicated in line 3-4 of the cam groove. Next is the return movement of the trigger forward toward its initial position; the first forward movement from position 4 to 5A causes the cam to rise to its highest position. Further relaxation of the trigger to open to position 5B causes the cam to drop all the way to its 5B position or its lowest position. Finally, complete return of the trigger from 5B to 5C or 1, in its fully open position, causes the driver to rise back to its half-way position. It is assumed that standard techniques for cam design would be used to establish the mathematical details of this cam shape which are symbolically indicated and represented by the figure "8" cam groove 40 in FIG. 3 and similarly represented by the diagram in FIG. 15. In going from position 2 to 3 for example, the driver drops; to cause this descent the near end 38 of lever 35 must rise. The cam 40 illustrated in FIG. 15 shows a drop from position 2 to 3 which is symbolic for clarity since the actual cam groove should rise.

Figure 16:
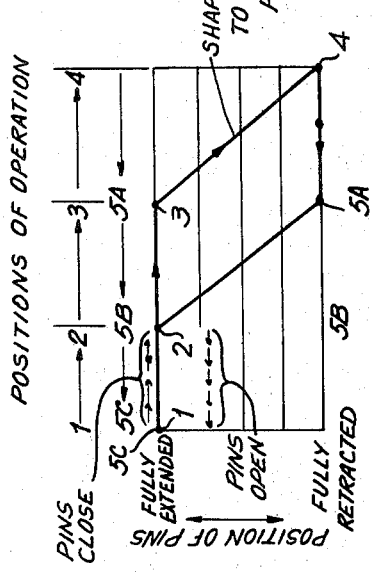
FIG. 16 is a graph showing a second cam configuration for the sequential movement of the trigger and corresponding movement of the pin sub-assemblies.

FIG. 16 is another graph which represents the coordinated movements of the trigger and pins, and correspondingly numbered steps of operation across the top, indicated as steps 1-4 to the right and steps 5A through 5C to the left. Vertical indicia indicate the movement of the four pins from their fully extended position shown at the top of the graph to their fully retracted position shown at the bottom. The explanation for this cam shape is generally similar to that presented above regarding FIG. 15. The movement of the trigger from position 1 to 2 shows that the cam line 1-2 is horizontal, so the pins remain in their fully extended state. Further squeezing of the trigger from positions 2-3 results in continued non-movement of the pins as indicated by the straight line of the cam 2-3. Additional squeezing of the trigger causes the pins to retract along the diagonal line shown in the diagram from positions 3-4. Now upon releasing the trigger to move counterclockwise toward its open position, the pins follow the path indicated from point 4 to 5A, and further expansion of the trigger causes the pins to quickly extend, along lines 5A to 5B. The final extension of the trigger in the handle from 5B to 5C or 1 does not change the fully extended position of the pins.

For convenience in terminology, control means may be used to include the lock and safety pins, the expansion or staple opening and closing pins, and the driver;

drive means may be used to include cams, followers, linkages, etc. interconnecting the trigger and the control means for actuating the components of the control means.

It should be noted that the expansion pins, while they move forward and backward with the safety and lock pins, also converge or diverge according to a specific program which is partly indicated in FIG. 16. When the trigger moves initially from position 1 to 2, the pins remain extended but they converge or close. Correspondingly when the trigger makes its final move from position 5B to 5C the pins, which are already extended, diverge or open and expand a staple which is in the ready position. This is further indicated by the difference between diagrams from FIGS. 9A and 4.

Figure 12:
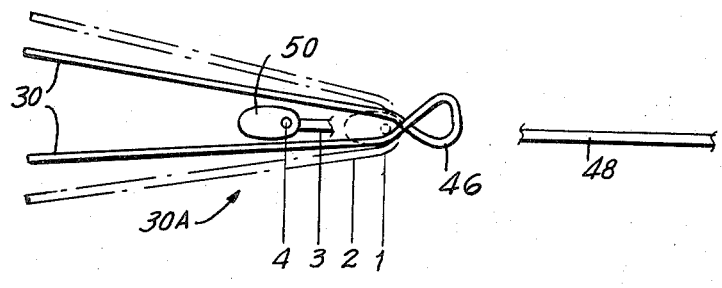
FIG. 12 is a top plan view of the expansion pin of FIG. 3.
Figure 13:
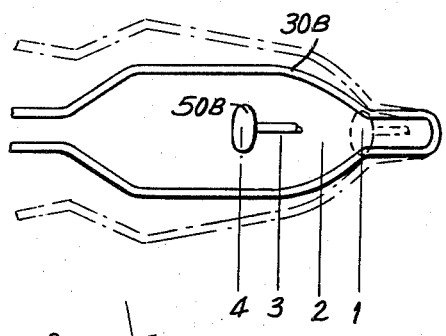
FIG. 13 is a top plan view of another embodiment of the expansion pin.

Opening and closing of the expansion pins was explained earlier with regard to wedge 50 and lever 48 as shown in FIGS. 12, 13, and 14. The pin member 30A in FIG. 12 and its alternate embodiment 30B in FIG. 13 are made of highly resilient material. In each case the natural state is closed, which corresponds to the natural state of the staples 21. The dotted configurations in these figures merely show the diverged or open condition when the wedge 50 or 50B respectively is in position 1. The wedge 50 does not need to be driven by a cam with a precisely defined pattern of movement, because it is sufficient to merely open or close the expansion pins; at all other times the wedge can be in clear space engaging nothing, while the trigger moves through its various other positions.

Figure 18:
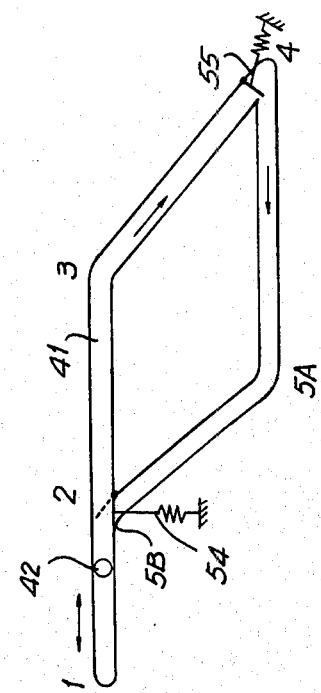
FIG. 18 is a schematic drawing showing a cam groove and follower corresponding to the cam movement of FIG. 16.
Figure 17:
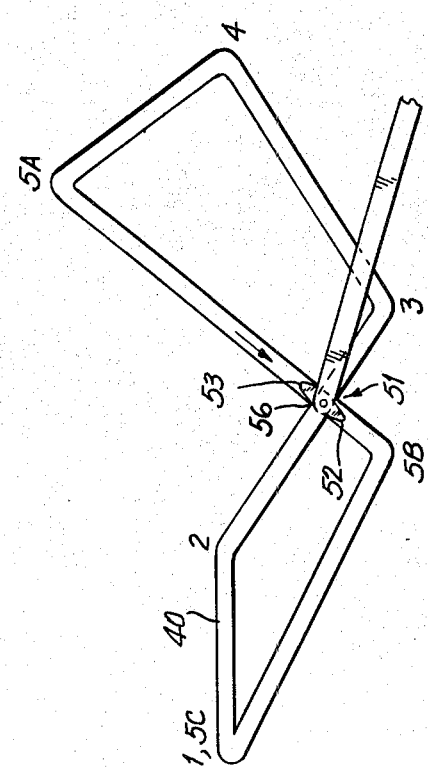
FIG. 17 is a schematic drawing showing a cam groove and follower corresponding to the cam movement of FIG. 15.

FIGS. 17 and 18 show details of the cam follower and cam groove associated with FIGS. 15 and 16 respectively. As was discussed earlier, when the trigger is pulled from positions 1 through 3 and approaches 4, it will emit a signal or provide some indication that the staple has fully closed as shown in FIG. 6A, and that further squeezing of the trigger will release the staple and disengage the device from the staple. Once the decision is made to continue squeezing the trigger and release is affectuated, a safety feature is provided so that the trigger must be fully released back to its original position before it can be compressed again, so that jamming with extra staples will be avoided. In order to prevent the follower from taking the wrong path on the cam, when it enters the intersection, a safety feature is provided in FIG. 17 by an elongated follower 56. Once this follower enters the intersection 51 of the grooves of the cam 40, the cam's nose part 52 will cross the intersection and enter the path toward position 5B before its tail section 53 has left the prior path. Accordingly, it is impossible for the follower to head for position 2 or 3 before first going to 5B, 5C(1), 2, etc.

A corresponding set of safety features are provided in the cam groove 41 in FIG. 18 which corresponds to cam groove 41 in FIG. 3. At points 2 and 4 are gates 54 and 55 each being spring-biased to remain closed. Accordingly, a follower 42 corresponding to follower 42 in FIG. 3 can move from position 1 to 3 in FIG. 18, but cannot move from position 1 to 5; also this follower could move from 5 to 4 to 3 past the gate 55. Finally of course the follower could move from position 5 through the gate 54 to position 2 and then back down to position 1. Obviously many alternative forms of gates are possible.

The apparatus shown in FIGS. 1–18 is perferably made of high quality materials suitable for use in a hospital operating room. The handle, trigger, housing, and certain internal parts are plastic, while the cams, followers, springs and staples and associated parts are appropriate metal. The staples 21 shown in FIGS. 3–9 obviously require very high strength along with very high resilience, properties which may be provided by various spring materials including the material Elgeloy ®. These staples have the natural, un-flexed state shown in FIGS. 3A and 5A, each staple being about one fourth the size illustrated herein, and each having sharp points on the opposing legs 21L indicated in FIGS. 5A and 6A. It is contemplated that the entire device could be manufactured so economically in view of its unusually small number of parts, and pre-loaded with a magazine full of staples, that it could be distributed as a disposable unit.

FIG. 19 illustrates one staple embodiment wherein each of the pointed ends comprises a bevelled edge which defines the same angle with a central or base axis x—x, so that the bevelled edges of the two ends of the staple in relaxed state are generally parallel.

The staples in their closed state may have various configurations wherein a wire is bent to circumscribe a space which may be oval, square, rectangular, circular, semi-circular, and elliptical, for example as illustrated in FIG. 20. These staples in their open and flexed state will be described as generally crescent shaped even though they will have various actual shapes corresponding to their closed shapes. The crescent concept simply means that in open configuration the pointed ends are spaced apart and directed generally transversely of the base of the staple, in contrast to the ends being directed toward each other in closed configuration. One example of the new staple is approximately 0.006 inch thick, 0.040 inch wide, and made of ELGELOY ® spring material made by the Elgeloy Corp. of America. A staple as shown in closed condition in FIGS. 3A and 9A is a continuous piece of wire having a top part 21Y, side parts extending generally downward from the top part, and legs 21L extending from said side parts toward each other, the legs being generally aligned with each other and terminating in pointed ends 21Q. Each of the side parts of the staple has a lower portion 21Z immediately adjacent a leg 21L. The lower portions 21Z are generally parallel in the closed condition of FIG. 9A. The closed staple in FIG. 9A has a maximum width dimension $W_1$ between the two side parts 21Z, and the staple in open condition in FIG. 4 has a distance $W_2$ between the ends 21Q that is greater than dimension $W_1$.

As seen in FIGS. 3, 3A, and 5B the staple magazine device comprises a bar 20 having front end 23 and an opposite rear end, which bar extends through and supports a plurality of staples aligned and supported thereon. Each staple has its top, side parts and legs extending around the bar or frame 20.

Obviously many variations of the staple and apparatus of this invention are possible within the scope and spirit of the disclosure and the claims appended hereto.

We claim:

1. A stapling device for delivering staples to an incision or wound to be closed and causing each of said delivered staples (i) to engage adjacent edges of tissue of the incision, (ii) to close and secure said edges together, and (iii) to separate from said device, where each of said staples is a resilient wire having pointed ends and bent to circumscribe a space, each staple having a relaxed closed configuration with said ends of the wire directed generally toward each other, each staple when flexed from said relaxed closed configuration to its open configuration defining a generally crescent shape, said flexed staple tending to return to its closed configuration, the device comprising:
(a) a housing including a staple discharge area,
(b) a handle,
(c) a trigger movable between a first position and a second position,
(d) a magazine in said housing for containing a plurality of said staples,
(e) control means comprising first, second, third and drive means, namely: first means for moving one staple at a time from said magazine to said discharge area,
second means for releasably engaging said staple in the discharge area, and
third means for controllably allowing a flexed staple in its open configuration to resiliently return to its closed configuration for joining adjacent edges of tissue to the extent that said staple closes itself, and
drive means interconnecting said trigger and said control means and operable by moving said trigger between said first and second positions, thereby causing said first, second and third means to operate as described and in the sequence listed above and subsequently causing said second means to disengage and discharge said closed staple from the device.

2. A device according to claim 1 wherein each staple moved to said discharge area is in closed and relaxed configuration, said third means is operated by said drive means to flex said closed staple in the discharge area to its open configuration before said third means allows said staple to engage adjacent edges of tissue of an incision and to close.

3. A device according to claim 2 or 3, further comprising spring means urging said trigger toward its just position, and thereby urging said third means to flex a staple in the discharge area to its open configuration.

4. A device according to claim 1 wherein said staples in said magazine and as delivered to said discharge area are in said closed relaxed configuration, said third means is operated by said drive means to flex each of said closed staples in the discharge area to its open configuration before said third means allows said staple to engage adjacent edges of tissue of an incision and to close.

5. A device according to claim 3 wherein said third means comprises a single pair of projections that are (a) positionable close together in the space circumscribed by a closed staple, (b) movable to diverge thereby flexing said closed staple to its open configuration, and (c) movable to converge thereby releasing said flexed staple to return to its closed configuration.

6. A device according to claims 1 or 3 wherein said drive means comprises first connection means having a near-end coupled to said trigger and far-end coupled to said first means, said drive means causing said first means to follow a prescribed first pattern of motion corresponding to movement of said trigger, whereby movement of the trigger from its second to first positions causes said first means to move one staple from the magazine to the discharge area.

7. A device according to claim 5 wherein said drive means further comprises a first cam carried by said trigger and a first cam follower operable with said first cam, and wherein said first connection means comprises first link means connecting said first cam follower with said first means.

8. A device according to claims 1 or 3 wherein each staple has a central arch part having top and bottom surfaces, and wherein said second means comprises a safety pin for engaging said bottom surface for temporarily preventing said staple from being disengaged from said device, and a lock pin for engaging said top surface for temporarily stabilizing and locking said staple between said safety and lock pins, said lock and safety pins being movable between a first position wherein they fixedly engage between them the central arch part of a staple, and a second position where the lock pin moves away from said safety pin, and both pins move away from the staple thereby releasing said staple to be discharged from said device.

9. A device according to claims 1 or 3 and wherein said drive means comprises second connection means having a near-end coupled to said trigger and a far-end coupled to said second and third means, said control means causing said second and third means to follow a prescribed second pattern of motion corresponding to movement of said trigger, whereby movement of the trigger from its second to first positions causes said second means to engage a staple delivered by said first means and causes said third means to flex said staple to its open position, and movement of said trigger from its first to second positions causes said third means to release said staple allowing it to resiliently return to its second position, and subsequently causes said second means to disengage and discharge said closed staple from said device.

10. A device according to claim 6 wherein said drive means further comprises a second cam carried by said trigger and a second cam follower operable with said second cam, and wherein said second connection means comprises second link means connecting said second cam follower with said second and third means.

11. A device according to claims 1 or 3 wherein said drive means permits reversability to the operation of said third means, thereby flexing said staple from its closed to its open configurations, said drive means further comprising signal means that provides a signal to the operator of the device when said third means has allowed said staple to reach its closed position but before said second means has disengaged and discharged said staple, thereby advising said operator he has the option of (a) reversing said third means to open said staple, or (b) continuing the operation of the device to disengage and discharge said staple.

12. A device according to claim 10 wherein said signal means is operated by said trigger and indicates a signal to the operator when said trigger is moved toward and almost reaches its second position.

13. A device according to claim 1 wherein said first means further comprises a driver that moves from a high position where it engages a staple from said magazine, to a low position where it delivers said staple to the discharge area.

14. A device according to claim 13 wherein said drive means causes said driver to descend to its low position, said driver then urging said staple to its fully closed position.

15. A device according to claims 1 or 3 wherein said control means is reversible, said trigger being movable toward its first position thereby causing said third means to flex and return said staple to its open configuration from its closed configuration before said second means has disengaged and discharged said staple from the device.

16. A device according to claim 15 further comprising spring means in said housing urging said trigger toward its open position, thereby urging said third means to flex a staple in the discharge area toward its open configuration.

17. In a surgical stapler device operable with surgical staples who configuration is variable between open and closed states, each staple being a continuous segment of wire comprising a top part having top and bottom surfaces, side parts extending generally downward from said top part, and legs extending from said side parts, said staple having a closed configuration wherein said legs extend generally toward each other and an open configuration wherein said legs are spaced apart and inclined from their closed configuration orientation, the device comprising a housing including a staple discharge area and a trigger movable in said housing between first and second positions, the improvement in combination therewith, comprising:
   (a) a magazine in said housing for holding a plurality of said staples in closed state,
   (b) first means for moving one staple at a time from said magazine to said discharge area,
   (c) control means in said housing for releasably engaging said moved staple in closed state in said discharge area and varying its configuration to open state, moving said open staple out of said discharge area to a location outside of said housing, further returning said staple configuration to closed state, and releasing said staple from said device, and
   (d) drive means for coupling said trigger to said control means, whereby movement of said trigger causes said control means to carry out the sequential steps defined in (c), and wherein said control means comprises lock means for selectively holding and releasing a staple, and staple opening and closing means for engaging and pressing said side parts and thereby bending said staple into its open configuration from its closed configuration and subsequently returning said staple to its closed configuration.

18. A surgical stapler according to claim 17 wherein said control means further comprises a driver movable between high and low positions for driving one staple at a time from said magazine into said discharge area, and for urging said staple into fully closed configurations as said staple opening and closing means returns said staple to its closed configuration.

19. A surgical stapler according to claim 18 wherein said lock means comprises a first pair of pins for temporarily engaging said top part of said staple, one pin for engaging said bottom surface thereof to prevent disengagement of the staple from the device of the other pin for engaging said top surface thereof to stabilize and lock said staple between said pins, and wherein said staple opening-and-closing means comprises a second pair of pins for temporarily engaging said side parts of said staple, said pins being movable to diverge from each other thereby bending said staple to its open configuration while said lock means stabilizes the staple and to subsequently converge thereby returning said staple to its closed configuration.

20. In a surgical stapler device operable with surgical staples whose configuration is variable between open and closed states, each staple being a continuous segment of wire comprising a top part having top and bottom surfaces, side parts extending from said top part, and legs extending from said side parts, said staple having a closed configuration wherein said legs extend generally toward each other and an open configuration wherein said legs are spaced apart and inclined from their closed configuration orientation, the device comprising a housing including a staple discharge area and a trigger movable in said housing between first and second positions, the improvement in combination therewith, comprising:
   (a) a magazine in said housing for holding a plurality of said staples in closed state,
   (b) first means for moving one staple at a time from said magazine to said discharge area,
   (c) control means in said housing for releasably engaging said moved staple in closed state in said discharge area and varying its configuration to open state, moving said open staple out of said discharge area to a location outside of said housing, further returning said staple configuration to closed state, and releasing said staple from said device, and
   (d) drive means for coupling said trigger to said control means, whereby movement of said trigger causes said control means to carry out the sequential steps carried out by said control means.

21. In a surgical stapler device operable with surgical staples whose configuration is variable between open and closed states, each staple being a continuous segment of wire comprising a top part having top and bottom surfaces, side parts extending generally downward from said top part, and legs extending from said side parts, said staple having a closed configuration wherein said legs extend generally toward each other and an open configuration wherein said legs are spaced apart and inclined from their closed configuration orientation, the device comprising a housing and a trigger movable in said housing between first and second positions, the improvement in combination therewith, comprising:
   (a) a magazine in said housing for holding a plurality of said staples in closed state,
   (b) first means for moving one staple at a time from said magazine to a control means,
   (c) control means in said housing for releasably engaging said moved staple in its closed state, varying the staple configuration to its open state, moving said open staple to a location outside of said housing, returning said staple configuration to its closed state, and releasing said staple from said device, and
   (d) drive means for coupling said trigger to said control means, whereby movement of said trigger causes said control means to carry out the sequential steps carried out by said control means.

22. A stapler according to any of claims 17, 20, or 21 wherein said staple has a maximum width dimension in its open state established as the maximum distance that can be defined between corresponding parts of the two legs of said staple, and said housing has a width dimension adjacent said staple and corresponding to and similarly oriented as said staple, said housing width dimension being less than said maximum width dimension of said staple when driven to its open state by said control means.

* * * * *

UNITED STATES PATENT AND TRADEMARK OFFICE
CERTIFICATE OF CORRECTION

PATENT NO. : 4,396,139
DATED : August 2, 1983
INVENTOR(S) : HALL, ET AL.

It is certified that error appears in the above—identified patent and that said Letters Patent is hereby corrected as shown below:

Column 7, line 47, change "39" to --30--.
Column 13, line 35, change "3" to --4--.
Column 13, line 36, change "just" to --first--.

Column 14, line 49, change "claim 10" to --claim 11--.
Column 16, line 48, after "moving" insert --at least a portion of--.

Signed and Sealed this

Eighth Day of October 1985

[SEAL]

Attest:

Attesting Officer

DONALD J. QUIGG

Commissioner of Patents and Trademarks—Designate